United States Patent

Broadhurst et al.

Patent Number: 6,066,662
Date of Patent: May 23, 2000

[54] HYDROXYLAMINE DERIVATIVES AND THEIR USE AS METALLOPROTEINASE INHIBITING AGENTS

[75] Inventors: Michael John Broadhurst, Royston; Paul Anthony Brown; William Henry Johnson, both of Hitchin, all of United Kingdom

[73] Assignee: Hoffmann-La Roche Inc., Nutley, N.J.

[21] Appl. No.: 08/737,947

[22] PCT Filed: May 23, 1995

[86] PCT No.: PCT/EP95/01955

§ 371 Date: Nov. 2, 1996

§ 102(e) Date: Nov. 2, 1996

[87] PCT Pub. No.: WO95/33709

PCT Pub. Date: Dec. 14, 1995

[30] Foreign Application Priority Data

Jun. 3, 1994 [GB] United Kingdom ............... 9411088

[51] Int. Cl.[7] .................. C07D 233/74; C07C 259/06; C07C 239/18

[52] U.S. Cl. .............. 514/384; 514/231.2; 514/235.5; 514/357; 514/422; 514/424; 514/425; 514/396; 514/359; 514/383; 514/384; 514/361; 548/300.1; 548/311.1; 548/314.7; 548/323.5; 548/315.7; 548/517; 548/518; 548/541; 548/543; 548/530; 548/546; 548/262.8; 548/263.2; 548/263.4; 548/263.6; 548/316.4; 548/317.1; 548/318.5; 548/397; 548/398; 544/106; 544/111; 546/184; 546/192; 546/207; 546/208

[58] Field of Search ............... 548/333.5, 311.1, 548/314.7, 315.7, 323.5, 517, 518, 262.2, 263.4, 300.1, 543, 546, 262.8, 263.2, 318.5, 317.1; 514/397, 396, 359, 398, 235.5, 425, 383, 384; 544/106, 111; 546/184, 192, 202, 208

[56] References Cited

U.S. PATENT DOCUMENTS 4,599,361  7/1986  Dickens et al. ............... 514/575
4,743,587  5/1988  Dickens et al. ............... 514/575
5,032,590  7/1991  Hübsch et al. ............... 514/248
5,183,900  2/1993  Galardy et al. ............... 548/495
5,189,178  2/1993  Galardy et al. ............... 548/495
5,239,078  8/1993  Galardy et al. ............... 546/201
5,268,384  12/1993 Galardy et al. ............... 514/419
5,304,549  4/1994  Broadhurst et al. ............. 514/80
5,691,381  11/1997 Jacobson et al. ............... 514/562

FOREIGN PATENT DOCUMENTS 0 231 081   8/1987   European Pat. Off. .
0 489 577   6/1992   European Pat. Off. .
0 489 579   6/1992   European Pat. Off. .
0489577     6/1992   European Pat. Off. .
0497192     8/1992   European Pat. Off. .
0 575 844   12/1993  European Pat. Off. .
0575844     12/1993  European Pat. Off. .
2268934     1/1994   United Kingdom .

OTHER PUBLICATIONS

English Abstract for Document B5.

*Primary Examiner*—S. Mark Clardy
*Assistant Examiner*—Sabiha N. Qazi
*Attorney, Agent, or Firm*—George W. Johnston; William H. Epstein; Lewis J. Kreisler

[57] ABSTRACT

The invention provides hydroxylamine derivatives of formula (I) wherein A, $R^1$, $R^2$ and $R^3$ have the significance given in the description, which are matrix metalloproteinase inhibitors and which also prevent TNF release. They are therefore useful for the control or prevention of degenerative joints diseases such as rheumatoid arthritis and osteoarthritis or for the treatment of invasive tumours, atherosclerosis or multiple sclerosis. They can be manufactured according to generally known methods.

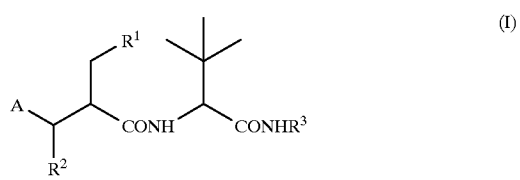

32 Claims, No Drawings

HYDROXYLAMINE DERIVATIVES AND THEIR USE AS METALLOPROTEINASE INHIBITING AGENTS

The present invention is concerned with hydroxylamine derivatives.

The hydroxylamine derivatives provided by the present invention are compounds of the general formula

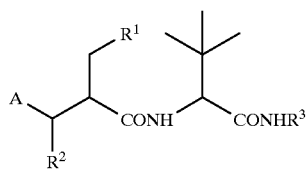
(I)

wherein

A represents a group of the formula

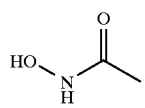
(a)

or

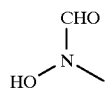
(b)

$R^1$ represents cyclopropyl, cyclobutyl or cyclopentyl;

$R^2$ represents hydrogen, hydroxy, lower alkyl or a group of the formula —$(CH_2)_n$-aryl or —$(CH_2)_n$-Het in which n stands for 1–4 and Het represents a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other carbon atoms by lower alkyl or oxo and/or on any additional N atom(s) by lower alkyl or aryl; and $R^3$ represents hydrogen or lower alkyl optionally substituted by aryl, amino, protected amino, di(lower alkyl) amino, guanidino, carboxyl, protected carboxyl, carbamoyl, pyrrolidino, piperidino or morpholino;

and pharmaceutically acceptable salts thereof.

The compounds of formula I possess valuable pharmacological properties. In particular, they are matrix metalloproteinase inhibitors and can also prevent TNF release. They can be used in the control or prevention of degenerative joint diseases such as rheumatoid arthritis and osteoarthritis or in the treatment of invasive tumours, atherosclerosis or multiple sclerosis.

Objects of the present invention are the compounds of formula I and their pharmaceutically acceptable salts per se and for use as therapeutically active substances; a process for the manufacture of said compounds and salts; intermediates useful in said process; medicaments containing said compounds and salts and the manufacture of these medicaments; the use of said compounds and salts in the control or prevention of illnesses or in the improvement of health, especially in the control or prevention of degenerative joint diseases or in the treatment of invasive tumours or atherosclerosis, or for the manufacture of a medicament for the control or prevention of degenerative joint diseases or for the treatment of invasive tumours, atherosclerosis or multiple sclerosis.

As used in this Specification, the term "lower" means that the group qualified thereby is a straight-chain or branched-chain group containing a maximum of 7, preferably a maximum of 4, carbon atoms. Examples of lower alkyl groups are methyl, ethyl, n-propyl, isopropyl, n-butyl, isobutyl, sec.butyl, tert.butyl, n-pentyl and n-hexyl. The term "aryl" means an optionally substituted phenyl or naphthyl group, with the substituent(s) being selected from halogen (i.e. fluorine, chlorine, bromine or iodine), trifluoromethyl, lower alkyl, lower alkoxy (e.g. methoxy, ethoxy, propoxy, isopropoxy, butoxy, tert.butoxy etc.), phenyl and the like.

The terms "protected amino" and "protected carboxy" mean amino and carboxy groups, respectively, which are protected in a manner known per se, e.g. as in peptide chemistry. Thus, an amino group can be protected by a benzyloxycarbonyl, tert. butoxycarbonyl, trifluoroacetyl or like group. A carboxy group can be protected in the form of a readily cleavable ester such as the methyl, ethyl, benzyl or like ester.

The compounds of formula I form pharmaceutically acceptable salts with bases such as alkali metal hydroxides (e.g. sodium hydroxide and potassium hydroxide), alkaline earth metal hydroxides (e.g. calcium hydroxide and magnesium hydroxide), ammonium hydroxide and the like. The compounds of formula I which are basic form pharmaceutically acceptable salts with acids. As such salts there come into consideration not only salts with inorganic acids such as hydrohalic acids (e.g. hydrochloric acid and hydrobromic acid), sulphuric acid, nitric acid, phosphoric acid etc, but also salts with organic acids such as acetic acid, tartaric acid, succinic acid, fumaric acid, maleic acid, malic acid, salicylic acid, citric acid, methanesulphonic acid, p-toluenesulphonic acid etc.

The compounds of formula I contain at least two asymmetric carbon atoms and can accordingly exist as optically active enantiomers, as diastereoisomers or as racemates. The present invention is intended to embrace all of these forms.

In the compounds of formula I above, A preferably represents a group of the formula (a).

$R^2$ preferably represents hydrogen, a group of the formula —$(CH_2)_n$-aryl, especially where the aryl group is unsubstituted phenyl, or a group of the formula —$(CH_2)_n$-Het, especially where Het optionally contains as additional hetero atom(s) one or two N atoms, one N atom and one O atom or one O atom. Examples of such groups denoted by Het are those of the formulae:

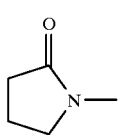
(a)

-continued

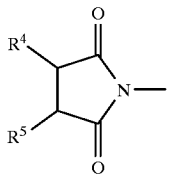
(b)

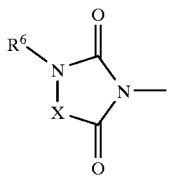
(c)

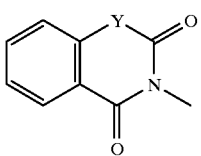
(d)

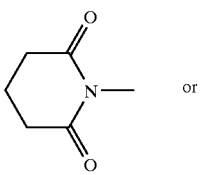
(e)

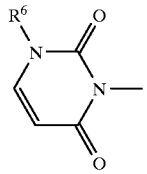 or
(f)

in which
R⁴ and R⁵ each represent hydrogen or together represent an additional bond or the remainder of a fused benzene ring;
R⁶ represents hydrogen, lower alkyl or aryl;
X represents —CO—, —CH₂—, —CH(lower alkyl)—, —C(lower alkyl)₂—, —NH—, —N(lower alkyl)— or —O—; or, when R⁶ represents lower alkyl and X represents —N(lower alkyl), the lower alkyl groups can be joined to form a 5-, 6- or 7-membered ring; and
Y represents —O—, —NH— or —N(1–6C alkyl)—.

In an especially preferred embodiment Het represents a group of formula (b), particularly phthalimido, or (c), particularly 3,4,4-trimethyl-2,5-dioxo-1-imidazolidinyl.

R³ preferably represents unsubstituted lower alkyl, especially methyl.

Particularly preferred compounds of formula I above are:
N2-[3-Cyclobutyl-2(R or S)-[(hydroxycarbamoyl)methyl]propionyl]-N1,3-dimethyl-L-valinamide,
N2-[3-cyclopropyl-2(R or S)-[(hydroxycarbamoyl)methyl]propionyl]-N1,3-dimethyl-L-valinamide,
N2-[3-cyclopentyl-2(R or S)-[(hydroxycarbamoyl)methyl]propionyl]-N1,3-dimethyl-L-valinamide,
N2-[3-cyclopropyl-2(R)-[1(R or S)-(hydroxycarbamoyl)-2-(3,4,4-trimethyl-2,5-dioxo-1-imidazolidinyl)ethyl]propionyl]-N1,3-dimethyl-L-valinamide and N2-[3-cyclobutyl-2(R)-[1(R or S)-(hydroxycarbamoyl)-2-(3,4,4-trimethyl-2,5-dioxo-1-imidazolidinyl)ethyl]propionyl]-N1,3-dimethyl-L-valinamide.

Other particularly preferred compounds of formula I are:
N2-[3-cyclobutyl-2(R)-[1(R or S)-(hydroxycarbamoyl)-4-phenyl-butyl]propionyl]-N1,3-dimethyl-L-valinamide and
N2-[3-cyclopentyl-2(R)-[1(R or S)-(hydroxycarbamoyl)-4-phenyl-butyl]propionyl]-N1,3-dimethyl-L-valinamide.

According to the process provided by the present invention, the compounds of formula I hereinbefore and their pharmaceutically acceptable salts are manufactured by
a) reacting an acid of the general formula

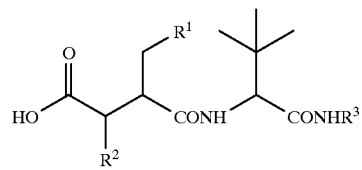
(II)

wherein R¹, R² and R³ have the significance given earlier, with a compound of the general formula

H₂NOZ   (III)

wherein Z represents hydrogen, tri(lower alkyl)silyl or diphenyl(lower alkyl)silyl,
and, where required, cleaving off any diphenyl(lower alkyl) silyl group present in the reaction product, or
b) catalytically hydrogenating a compound of the general formula

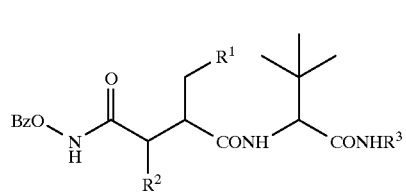
(IV)

wherein R¹, R² and R³ have the significance given earlier and Bz represents benzyl, or
c) reacting a hydroxylamine of the general formula

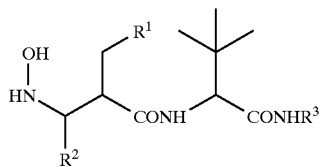
(V)

wherein R¹, R² and R³ have the significance given earlier, with formic acid and acetic anhydride and, where required, treating the reaction product with an inorganic base, and, if desired, converting a compound of formula I obtained into a pharmaceutically acceptable salt.

The reaction of an acid of formula II with a compound of formula III in accordance with embodiment (a) of the process can be carried out in a known manner, for example in an inert organic solvent such as dichloromethane, dimethylformamide or the like using hydroxybenzo-triazole in the presence of a condensation agent such as 1-ethyl-3-(3- dimethylaminopropyl)carbodiimide hydrochloride at about 0° C. to about room temperature. Preferred compounds of formula III are those in which Z represents tert.butyldimethylsilyl or tert.butyldiphenylsilyl. When a compound of formula III in which Z represents tri(lower alkyl)silyl is used, this group is cleaved off during the reaction and working-up, and a compound of formula I is obtained directly. On the other hand, when a compound of formula III in which Z represents diphenyl(lower alkyl)silyl is used, this group remains in the reaction product and must subsequently be cleaved off in a known manner, for example by means of fluoride ions.

The catalytic hydrogenation of a compound of formula IV in accordance with embodiment (b) of the process can be carried out in a manner known per se; for example in an inert organic solvent using hydrogen in the presence of a noble metal catalyst. Suitable inert organic solvents are, for example, lower alkanols such as methanol, ethanol, etc. With respect to the catalyst, this can be, for example, a platinum, palladium or rhodium catalyst which can be supported on a suitable carrier material. Palladium-on-charcoal is the preferred catalyst. The temperature and pressure are not critical, although for convenience the catalytic hydrogenation is preferably carried out at room temperature and under atmospheric pressure.

Embodiment c) of the process is conveniently carried out by adding a hydroxylamine of formula V to a mixture of formic acid and acetic anhydride, especially a 1:1 mixture by volume, at about room temperature. The reaction product contains, or comprises mainly, the 0-acetate corresponding to formula I [A=group (b)] and is converted into the desired compound of formula I by treatment with an inorganic base, especially an alkali metal bicarbonate such as sodium or potassium carbonate. This treatment is suitably carried out in a lower alkanol, preferably methanol.

Compounds of formula I can be converted into pharmaceutically acceptable salts by treatment with bases and basic compounds of formula I can be converted into pharmaceutically acceptable salts by treatment with acids. Such treatments can be carried out in a conventional manner.

The acids of formula II which are used as starting materials in embodiment (a) of the process are novel and form a further object of the present invention. The acids of formula II in which $R^2$ represents hydroxy, lower alkyl or a group of the formula $-(CH_2)_n$-aryl or $-(CH_2)_n$-Het can be prepared, for example, as illustrated in Reaction Scheme I hereinafter in which $R^1$, $R^3$ and Bz have the significance given earlier, $R^{21}$ represents hydroxy, lower alkyl or a group of the formula $-(CH_2)_n$-aryl or $-(CH_2)_n$-Het and tBu represents tert.butyl:

Reaction Scheme 1

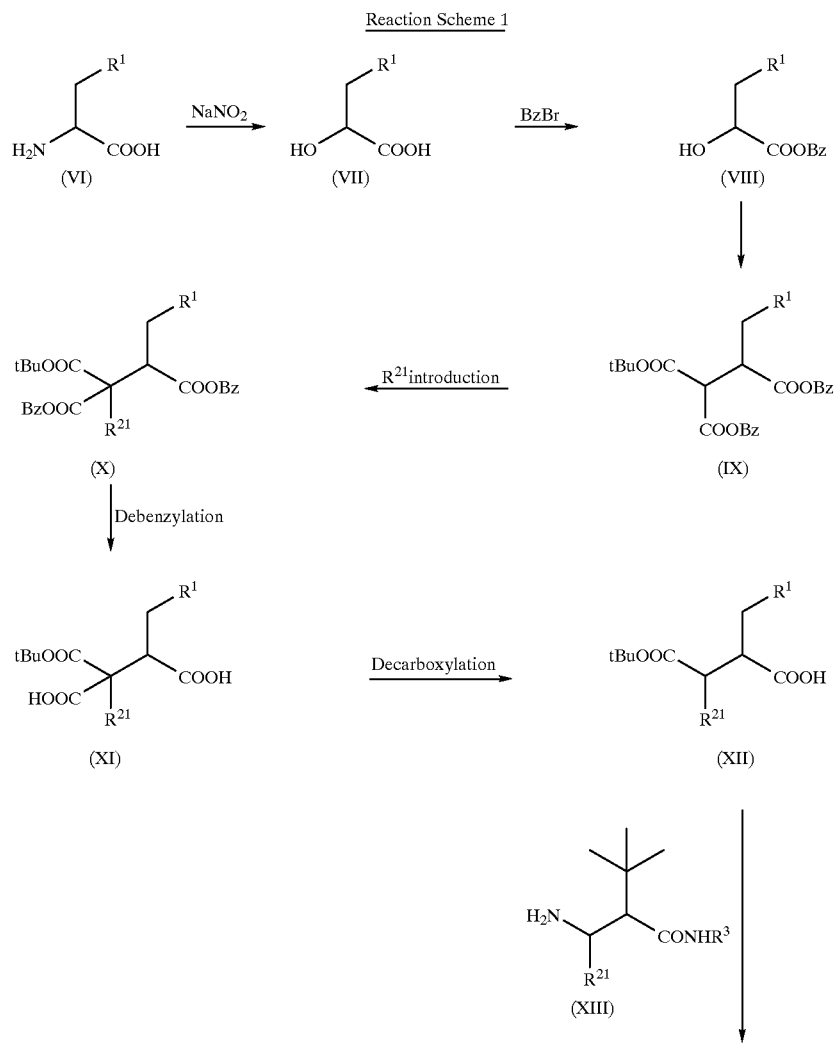

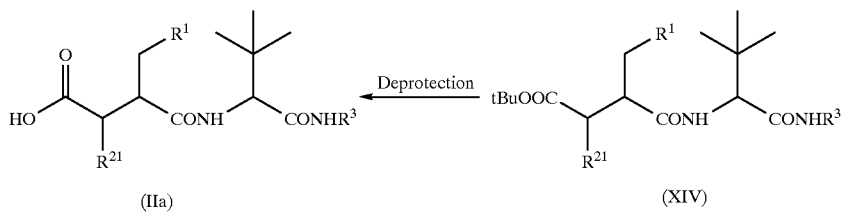

Having regard to Reaction Scheme I, the individual steps thereof can be carried out according to methods known per se. Thus, in the first step, an amino acid of formula VI, which can be obtained according to the procedure described by Chenault H. K, Dahmer J. and Whitesides G. M., J.Am. Chem. Soc. 1989, 111, 6354–6364, is converted by treatment with sodium nitrite in the presence of concentrated sulphuric acid into a hydroxy acid of formula VII which is subsequently reacted with benzyl bromide in the presence of an organic base, e.g. a trialkylamine such as triethylamine, into a corresponding benzyl ester of formula VIII. The latter is then activated, e.g. by reaction with trifluoromethanesulphonic anhydride, and treated with benzyl tert-butyl malonate in the presence of a strong base, e.g. an alkali metal hydride such as sodium hydride, to give a compound of formula IX. The group $R^{21}$ is then introduced into the compound of formula IX either by treatment with a strong base, e.g. an alkali metal hydride such as sodium hydride, and reaction with a compound of the formula $R^{22}Br$, wherein $R^{22}$ represents lower alkyl or a group of the formula —$(CH_2)_n$-aryl or —$(CH_2)_n$-Het, or by reaction with oxodiperoxymolybdenum(pyridine) hexamethylphosphoramide in order to introduce a hydroxy group. The resulting dibenzyl tert-butyl butanetricarboxylate of formula X is then debenzylated by catalytic hydrogenation, e.g. in the presence of a palladium catalyst such as palladium-on-charcoal, to give a tert-butyl dihydrogen butanetricarboxylate of formula XI. Decarboxylation of this compound, e.g. by heating in toluene with triethylamine, which may be carried out in situ, yields a tert-butyl hydrogen succinate of formula XII which is condensed with an amine of formula XIII, e.g. using 1-hydroxybentriazole in the presence of a condensation agent such as 1-ethyl-3-(3-dimethylaminopropyl)carbodiimide hydrochloride, to give a compound of formula XIV which is deprotected (e.g. by treatment with trifluoroacetic acid) to give an acid of formula IIa.

The acids of formula II in which $R^2$ represents hydrogen can be prepared, for example, as illustrated in Reaction Scheme II hereinafter in which $R^1$, $R^3$, Bz and tBu have the significance given earlier:

Reaction Scheme II

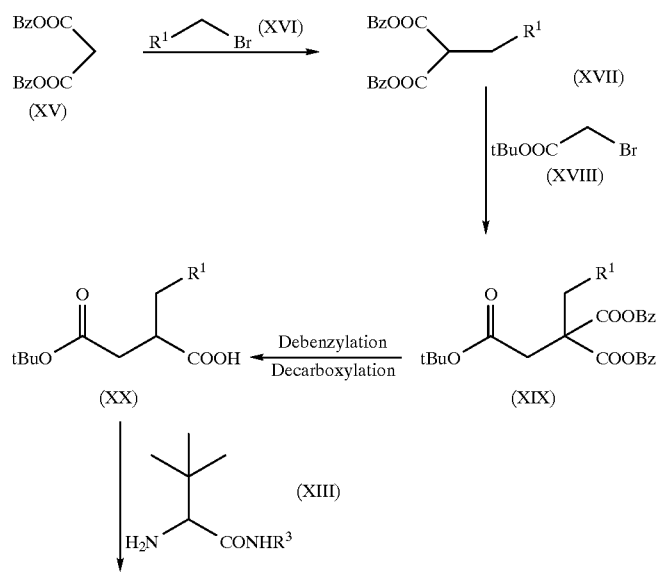

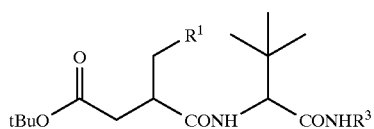

(XXI)

↓ Deprotection

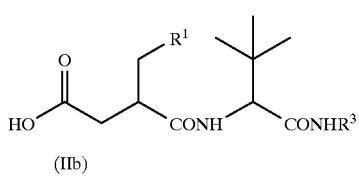

(IIb)

Having regard to Reaction Scheme II, the individual steps of which can be carried out according to methods known per se, the first step comprises reacting dibenzyl malonate of formula XV, which is a known compound, with an appropriate cycloalkyl-methyl bromide of formula XVI, which is also a known compound, to give a compound of formula XVII. The latter is then reacted with tert.butyl bromoacetate of formula XVIII and the resulting compound of formula XIX is converted into an acid of formula IIb by debenzylation and decarboxylation, condensation with a compound of formula XIII and finally deprotection in a manner analogous to that described in connection with Reaction Scheme I.

The compounds of formula IV which are used as starting materials in embodiment (b) of the process are novel and form a further object of the present invention.

The compounds of formula IV can be prepared, for example, by reacting an acid of formula II with O-benzylhydroxylamine. This reaction can be carried out in a known manner, for example in an inert organic solvent such as dichloromethane or dimethylformamide using hydroxybenzotriazole in the presence of a condensation agent such as 1-ethyl-3-(3-dimethyl-aminopropyl) carbodiimide hydrochloride.

The compounds of formula V which are used as starting materials in embodiment c) of the process are novel and form a further object of the present invention.

The compounds of formula V can be prepared, for example, as illustrated in Reaction Scheme III hereinafter in which $R^1$, $R^2$ and $R^3$ have the significance given earlier:

Reaction Scheme III

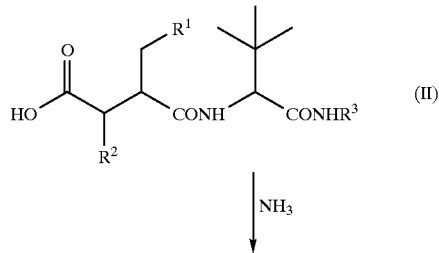

(II)

↓ NH₃

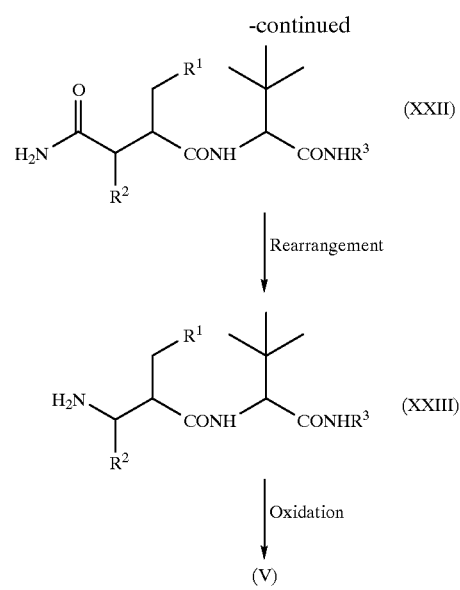

In the first step of Reaction Scheme III an acid of formula II in an inert solvent, e.g. dichloromethane or dimethylformamide, can be treated with the ammonium salt of 1-hydroxybenzotriazole in the presence of a tertiary amine such as N-ethylmorpholine and a condensation agent such as 1-ethyl-3-(3-dimethylaminopropyl)carbodiimide hydrochloride, suitably at about 0° C. to room temperature, to give an amide of formula XXII. This amide can then be rearranged in the second step in a Hofmann reaction, for example by treatment with bis[(trifluoroacetoxy)iodo] benzene in aceto-nitrile/water, suitably at about room temperature and under an inert gas such as nitrogen. The resulting amine of formula XXIII can subsequently be converted into the desired hydroxylamine starting material of formula V by treatment with an oxidizing agent such as 3-chloroperbenzoic acid, 1,1-dimethyldioxirane or 1-trifluoromethyl-1-methyldioxirane at a low temperature, e.g. about −78° C.

As mentioned earlier, the compounds of formula I and their pharmaceutically acceptable salts are matrix metalloproteinase inhibitors.

The inhibitory activity against one such enzyme, collagenase, can be demonstrated using the test procedure described hereinafter:

This test demonstrates the in vitro collagenase inhibiting activity and is carried out using collagenase obtained from a culture of human synovial fibroblasts according to the method of Dayer J-M et al., Proc. Natl. Acad. Sci. USA (1976), 73 945, following activation of the procollagenase in the conditioned medium by treatment with trypsin. Collagenase activity was measured using $^{14}$C-acetylated collagen type I from rat tail tendons as the substrate and employing the microtitre plate assay method of Johnson-Wint, B, Anal. Biochem. (1980), 104, 175. The $IC_{50}$ is that concentration of a test compound in the enzyme digestion which reduces substrate cleavage and solubilization to 50% of that achieved by the enzyme alone.

The results obtained in the foregoing test with representative hydroxamic acid derivatives provided by this invention are compiled in the following Table:

TABLE

| Compound of Example No | Test A $IC_{50}$ (nM) |
| --- | --- |
| 1 | 2.0 |
| 2 | 7.0 |
| 3 | 5.0 |
| 4 | 1.0 |
| 5 | 1.0 |

The compunds of formula I and their pharmaceutically acceptable salts can be used as medicaments, for example in the form of pharmaceutical preparations. The pharmaceutical preparations can be administered orally, e.g. in the form of tablets, coated tablets, dragées, hard and soft gelatine capsules, solutions, emulsions or suspensions. However, they ca also be administered rectally, e.g. in the form of suppositories, or parenterally, e.g. in the form of injection solutions.

For the manufacture of pharmaceutical preparations the compounds of formula and their pharmaceutically acceptable salts can be formulated with therapeutically inert, inorganic or organic carriers. Lactose, corn starch or derivatives thereof, talc, stearic acid or its salts can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active ingredient no carriers are, however, generally required in the case of soft gelatine capsules. Suitable carriers for the manufacture of solutions and syrups are, for example, water, polyols, saccharose, invert sugar, glucose and the like. Suitable carriers for the manufacture of injection solutions are, for example, water, alcohols, polyols, glycerine, vegetable oils and the like. Natural and hardened oils, waxes, fats, semi-liquid polyols and the like are suitable carriers for the manufacture of suppositories.

The pharmaceutical preparations can also contain preservatives, stabilizers, wetting agents, emulsifiers, sweeteners, colorants, flavorants, salts for adjustment of the osmotic pressure buffers coating agents or antioxidants.

Medicaments containing a compound of formula I or a pharmaceutically acceptable salt thereof and a therapeutically acceptable carrier as well as a process for the manufacture of such medicaments are also objects of the present invention. This process comprises mixing a compound of formula I or a pharmaceutically acceptable salt thereof with a therapeutically inert carrier material and bringing the mixture into a galenical administration form.

As mentioned earlier, the compounds of formula I and their pharmaceutically acceptable salts can be used in the control or prevention of illnesses, especially in the control or prevention of degenerative joint diseases or in the treatment of invasive tumours, atherosclerosis or multiple sclerosis. The dosage can vary within wide limits and will, of course, be adjusted to the individual requirements in each particular case. In general, in the case of administration to adults, a daily dosage of from about 5 mg to about 30 mg, preferably from about 10 mg to about 15 mg, should be appropriate, although the upper limit may be exceeded when this is found to be expedient. The daily dosage can be administered as a single dosage or in divided dosages.

The following Examples illustrate the present invention.

EXAMPLE 1

A solution of 0.36 g of N2-[2(R or S)-[(benzyloxycarbamoyl)methyl]-3-cyclobutylpropionyl]-N1,3-dimethyl-L-valinamide (diastereoisomer 1) in 10 ml of methanol was hydrogenated in the presence 0.05 g of 5% palladium on charcoal for 1½ hours. The catalyst was removed by filtration and the solution was evaporated. The resulting solid was washed with 2 ml of cold methanol to give 0.19 g of N2-[3-cyclobutyl-2(R or S)-[(hydroxycarbamoyl)-methyl]propionyl]-N1,3-dimethyl-L-valinamide (diastereoisomer 1) as a white solid.

nmr ($d_4$ MeOH): 4.18(s,1H); 2.8–2.72 (m,1H); 2.7 (s,3H); 2.34–2.1 (m,3H); 2.09–2.02 (m,1H); 1.98–1.9 (m,1H); 1.85–1.54 (m,5H); 1.5–1.43 (m,1H); 0.96 (s,9H). MS 328 $(M+H)^+$.

The starting material was prepared as follows:

(i) 1.1 g of 80% sodium hydride dispersion in mineral oil were added portionwise to a stirred solution of 10.02 g of dibenzyl malonate in 100 ml of 1,2-dimethoxyethane under nitrogen. After the effervescence had subsided a solution of 5 g of cyclobutylmethyl bromide in 10 ml of 1,2-dimethoxyethane was added. The solution was heated at 60° C. overnight and then left to cool. The solvent was removed by evaporation to leave an oil which was redissolved in 100 ml of ethyl acetate. The solution was washed with water and then dried over anhydrous magnesium sulphate. The solvent was removed by evaporation to leave a pale yellow oil. Flash chromatography on silica gel using 10% ethyl acetate in hexane for the elution gave 1.83 g of dibenzyl cyclobutylmethyl malonate.

MS 353 $(M+H)^+$.

Rf [hexane/ethyl acetate (9:1)]=0.57.

(ii) 0.15 g of sodium hydride dispersion in mineral oil was added to a stirred solution of 1.65 g of dibenzyl cyclobutylmethyl malonate in 10 ml of 1,2-dimethoxyethane under nitrogen. The mixture was stirred at room temperature for 1.25 hours and then a solution of 0.96 g of tert-butyl bromoacetate in 1 ml of 1,2-dimethoxyethane was added. The solution was stirred at room temperature overnight and then the solvent was removed by evaporation. The residual oil was redissolved in ethyl acetate, washed with water, saturated sodium chloride solution and then dried over anhydrous magnesium sulphate. The solvent was removed to give 1.12 g of 2,2-dibenzyl 3-tert-butyl 1-cyclobutyl-2-propanetricarboxylate as an oil which was used without further purification.

MS 467 $(M+H)^+$.

Rf [hexane/ethyl acetate (4:1)]=0.64.

(iii) A solution of 2.1 g of 2,2-dibenzyl 3-tert-butyl 1-cyclobutyl-2-propanetricarboxylate in 20 ml of propan-2-ol was hydrogenated in the presence of 200 mg of 5% palladium on charcoal for 2 hours. The catalyst was removed by filtration and the solvent was evaporated to leave a colourless oil which was redissolved in 25 ml of toluene. 0.62 ml of triethylamine was added and the solution was heated at reflux for 1.25 hours. The mixture was cooled, diluted with 75 ml of toluene and washed with 2M hydrochloric acid. The organic layer was dried over anhydrous magnesium sulphate and evaporated to leave 1.14 g of 4-tert-butyl hydrogen 2(RS)-(cyclobutylmethyl)succinate as a colourless oil which was used without further purification.

MS 243 (M+H)$^+$.

Rf [dichloromethane/methanol (9:1)]=0.63.

(iv) 0.69 g of 1-hydroxybenzotriazole, 0.87 g of 1-ethyl-3-(3-dimethyl-aminopropyl)carbodiimide hydrochloride and 1.05 ml of N-ethylmorpholine were added to a stirred solution of 1 g of 4-tert-butyl hydrogen 2(RS)-(cyclobutylmethyl)succinate in 25 ml of dichloromethane at 0° C. The mixture was stirred at 0° C. for 1 hour and then 0.71 g of (S)-tertbutylglycine methylamide was added. The mixture was stirred at 0° C. for 1 hour and then at room temperature overnight. The mixture was diluted with 100 ml of dichloromethane and washed in succession with 5% sodium hydrogen carbonate solution, 2M hydrochloric acid solution and saturated sodium chloride solution. The organic layer was dried over anhydrous magnesium sulphate. The solvent was removed by evaporation to give 1.37 g of N2-[2(RS)[tert-butoxycarbonylmethyl]-3-cyclobutylpropionyl]-N1,3-dimethyl-L-valeramide as a 1:1 mixture of diastereoisomers in the form of a white foam.

nmr (CDCl$_3$): 6.68–6.6 (m,0.5H); 6.5–6.42 (m,1H); 6.25 (d,J=9,0.5H); 4.31 (d,J=8,0.5H); 4.26 (d,J=8,0.5H); 2.85 (d,J=4,1.5H); 2.78 (d,J=4,1.5H); 2.7–1.5 (m,12H); 1.45 (s,4.5H); 1.43 (s,4.5H); 1.08 (s,4.5H); 1.00 (s,4.5H).

MS 369 (M+H)$^+$.

(v) A solution of 1.37 g of N2[2(RS)[tert-butoxycarbonylmethyl]-3-cyclobutylpropionyl]-N1,3-dimethyl-L-valinamide as a 1:1 mixture of diastereoisomers in 20 ml of trifluoroacetic acid was stirred at room temperature for 2.5 hours. The solvent was removed by evaporation to leave an oil which was partitioned between diethyl ether and 5% sodium hydrogen carbonate solution. The aqueous phase was acidified with hydrochloric acid and extracted with dichloromethane. The organic layer was dried over anhydrous magnesium sulphate and then evaporated to give 1.2 g of N2-[2(RS)[carboxymethyl]-3-cyclobutylpropionyl]-N1,3-dimethyl-L-valinamide as a 1:1 mixture of diastereoisomers in the form of a white foam.

MS 313 (M+H)$^+$.

(vi) 0.59 g of 1-hydroxybenzotriazole, 0.74 g of 1-ethyl-3-(3-dimethyl-aminopropyl)carbodiimide hydrochloride and 0.89 ml of N-ethylmorpholine were added to a stirred solution of 1.1 g of N2-[2(RS)[carboxymethyl]-3-cyclobutylpropionyl]-N1,3-dimethyl-L-valinamide in 20 ml of dichloro-methane at 0° C. The mixture was stirred at 0° C. for 1 hour and then a solution of 0.54 g of O-benzylhydroxylamine in 1 ml of dichloromethane was added. The mixture was stirred at OOC for 1 hour and then at room temperature overnight. The solution was diluted with 50 ml of dichloro-methane, washed in succession with 5% sodium hydrogen carbonate solution and 2M hydrochloric acid and then dried over anhydrous magnesium sulphate. The solvent was evaporated to leave 1.08 g of a white foam. Flash chromatography on silica gel using 2% methanol in ethyl acetate for the elution gave 0.39 g of N2-[2(R or S)-[(benzyloxycarbamoyl)-methyl]-3-cyclobutylpropionyl]-N1,3-dimethyl-L-valinamide (diastereoisomer 1) in the form of a white foam and 0.44 g of N2-[3-cyclobutyl-2(R or S)-[(benzyloxycarbamoyl)methyl]propionyl]-N1,3-dimethyl-L-valanamide (diastereoisomer 2) in the form of a white foam.

Diastereoisomer 1.

nmr (CDCl$_3$): 9.5 (bs,1H); 7.32–7.23 (m,5H); 6.9 (d,J=9, 1H); 6.7 (bs,1H); 4.81 (s,2H); 2.89–2.81 (m,1H); 2.74–2.65 (m,4H); 2.38–2.30 (m,1H); 2.18–2.10 (m,2H); 2.01–1.8 (m,2H); 1.76–1.38 (m,5H); 0.9 (s,9H).

MS 418 (M+H)$^+$.

EXAMPLE 2

In a manner analogous to that described in the first paragraph of Example 1, from 2.3 g of N2-[2(R or S)-[(benzyloxycarbamoyl)methyl]-3-cyclopropylpropionyl]-N1,3-dimethyl-L-valinamide (diastereoisomer 1), prepared in a manner analogous to that described in Example 1(i)-(vi), there were obtained 1.69 g of N2-[3-cyclopropyl-2(R or S)-[(hydroxycarbamoyl)-methyl]propionyl]-N1,3-dimethyl-L-valinamide (diastereoisomer 1) as an off-white solid.

nmr (d$_4$ MeOH): 4.24 (s,1H); 3.0–2.92 (m,1H); 2.71 (s,3H); 2.36 (dd,J=13,7,1H); 2.22 (dd,J=13,6,1H); 1.4–1.32 (m,2H); 0.98 (s,9H); 0.78–0.6 (m,1H); 0.45–0.38 (m,1H); 0.36–0.31 (m,1H); 0.05- -0.03 (m,2H) MS 314 (M+H)$^+$.

EXAMPLE 3

In a manner analogous to that described in the first paragraph of Example 1, from 1 g of N2-[2(R or S)-[(benzyloxycarbamoyl))methyl]-3-cyclopentylpropionyl]-N1,3-dimethyl-L-valinamide (diastereoisomer 1), prepared in a manner analogous to Example 1(i)–(vi), there was obtained 0.79 g of N2-[3-cyclopentyl-2(R or S)-[(hydroxycarbamoyl)methyl]propionyl]-N1-3-dimethyl-L-valinamide (diastereoisomer 1) as a white solid.

nmr (d$_4$ MeOH): 4.2 (s,1H); 2.92–2.85 (m,1H); 2.68 (s,3H); 2.3 (dd,J=14,9,1H); 2.17 (dd,J=14,6,1H); 1.88–1.78 (m,1H); 1.74-1.28 (m,10H); 1.15-1.02 (m,1H); 0.97 (s,9H).

MS 342 (M+H)$^+$.

EXAMPLE 4

A solution of 0.47 g of N2-[2(R)-[1(R or S)-(benzyloxycarbamoyl)-2-(3,4,4-trimethyl-2,5-dioxo-1-imidazolidinyl)ethyl]-3-cyclopropylpropionyl]-N1,3-dimethyl-L-valinamide (as a 6:1 mixture of diastereoisomers) in 10 ml of ethanol was hydrogenated in the presence of 0.17 g of 5% palladium on charcoal for 5 hours. The catalyst was removed by filtration and the solvent was evaporated to leave a solid. Flash chromatography on silica gel using 5% methanol in dichloromethane for the elution gave 0.23 g of N2-[3-cyclopropyl-2(R)-[1(R or S)-(hydroxycarbamoyl)-2-(3,4,4-trimethyl-2,5-dioxo-1-imidazolidinyl)ethyl]propionyl]-N1,3-dimethyl-L-valinamide (diastereoisomer 1) as a white solid.

nmr (d$_4$ MeOH): 4.37 (s,1H); 3.9–3.85 (m,1H); 3.43 (dd, J=14,4,1H); 2.9 (s,3H); 2.88–2.83 (m,2H); 2.75 (s,3H); 1.45–1.32 (m,8H); 1.08 (s,9H); 0.66–0.57 (s,1H); 0.46–0.40 (m,1H); 0.38–0.32 (m,1H); 0.05- -0.03 (m,2H);

MS 468 (M+H)$^+$.

The starting material was prepared as follows:

(i) A solution of 4.9 g of 2(R)-amino-3-cyclopropylpropionic acid (prepared in a manner analogous to that described by Chenault H. K., Dahmer J. and Whitesides G. M. in J. Am. Chem. Soc. 1989, 111, 6354–6364) in 50 ml of water containing 4.05 ml of concentrated sulphuric acid was warmed to 45°. A solution of 10.5 g of sodium nitrite in 20 ml of water was added dropwise over 30 minutes. The solution was stirred at 45° for 4 hours and then cooled to room temperature. The solution was extracted with three 50 ml portions of ethyl acetate. The combined extracts were washed with water and dried over anhydrous magnesium sulphate. The solvent was evaporated to leave 3.95 g of a yellow oil containing 3-cyclopropyl-2(R)-hydroxypropionic acid which was used in the next step without further purification.

Rf [dichloromethane/methanol (9:1)]=0.65.

(ii) A solution of 3.95 g of 3-cyclopropyl-2(R)-hydroxypropionic acid in 50 ml of ethyl acetate was treated with 5.32 ml of triethylamine and 3.8 ml of benzyl bromide. The mixture was stirred and heated under reflux for 3 hours, then allowed to cool to room temperature overnight. The suspension was washed with 2M hydrochloric acid, water and saturated sodium chloride solution. After drying over anhydrous magnesium sulphate the solvent was evaporated. The residue was purified by flash chromatography on silica gel using hexane/ethyl acetate (2:1) for the elution to give 3.36 g of benzyl 3-cyclopropyl-2(R)-hydroxypropionate in the form of a yellow oil.

nmr (CDCl$_3$): 7.39–7.28 (m; 5H); 5.19 (d, 1H, J=14); 5.15 (d, 1H, J=14); 4.31–4.24 (m, 1H); 2.81 (br. d, IH); 1.69–1.54 (m, 2H); 0.87–0.74 (m, 1H); 0.45–0.34 (m, 2H); 0.08- -0.07 (m, 2H).

(iii) A solution of 3.36 g of benzyl 3-cyclopropyl-2(R)-hydroxypropionate and 1.49 ml of pyridine in 10 ml of dichloromethane was added dropwise to a solution of 3.07 ml of trifluoromethanesulphonic anhydride in 15 ml of dichloromethane at 0° over 30 minutes with stirring. The mixture was stirred at 0° for 2 hours and then washed with water and saturated sodium chloride solution. After drying over anhydrous magnesium sulphate the solvent was evaporated to give 5.37 g of benzyl 3-cyclopropyl-2(R)-trifluoro-methylsulphonyloxypropionate in the form of an orange oil which was used in the next step without further purification.

Rf [hexane/ethyl acetate (4:1)]=0.5.

(iv) A solution of 3.8 g of benzyl tert-butyl malonate in 50 ml of 1,2-dimethoxyethane was treated with 0.504 g of an 80% dispersion of sodium hydride in mineral oil. The mixture was stirred at room temperature for 30 minutes and then cooled to 0°. A solution of 5.37 g of benzyl 3-cyclopropyl-2(R)-trifluoromethylsulphonyloxypropionate in 20 ml of dichloromethane was added dropwise at 0°. The mixture was stirred at 0° for 2 hours and then left to warm to room temperature overnight. The solvent was evaporated and the residue was dissolved in ethyl acetate. The solution was washed with water and saturated sodium chloride solution. After drying over anhydrous magnesium sulphate the solvent was evaporated to give 6.54 g of 2,3-dibenzyl 3-tert-butyl 1-cyclopropyl-2(R),3(R,S),3-propane-tricarboxylate as a 1:1 mixture of diastereoisomers in the form of an orange oil.

nmr (CDCl$_3$): 7.46–7.36 (m, 20H); 5.19–5.07 (m, 8.H); 3.89 (d, 1H, J=10); 3.85 (d, 1H, J=10) 3.37–3.26 (m, 2H); 1.68–1.52 (m, 2H); 1.52–1.38 (m, 2H); 1.41 (s, 9H); 1.39 (s, 9H); 0.79–0.63 (m, 2H); 0.49–0.38 (m, 4H); 0.12- -0.07 (m, 4H).

(v) A solution of 6.4 g of 2,3-dibenzyl 3-tert-butyl 1-cyclopropyl-2(R),3(R,S),3-propanetricarboxylate (1:1 mixture of diastereoisomers) in 30 ml of 1,2-dimethoxyethane was treated with 0.446 g of an 80% dispersion of sodium hydride in mineral oil. The mixture was stirred at room temperature for 30 minutes. A solution of 3.84 g of 1-(bromomethyl)-3,4,4-trimethyl-2,5-imidazolinedione in 20 ml of 1,2-dimethoxyethane was added dropwise over 15 minutes. The mixture was stirred at room temperature for 36 hours, the solvent was evaporated and the residue was dissolved in ethyl acetate and washed with water and saturated sodium chloride solution. After drying over anhydrous magnesium sulphate the solvent was evaporated. The residue was purified by flash chromatography on silica gel using hexane/ethyl acetate (7:3) and subsequently hexane/ethyl acetate (6:4) for the elution to give 6.4 g of 2,3-dibenzyl 3-tert-butyl 1-cyclopropyl-4-(3,4,4-trimethyl-2,5-dioxo-1-imidazolidinyl)-2(R),3(R,S),3-butanetricarboxylate as a 1:1 mixture of diastereoisomers in the form of a clear oil.

nmr (CDCl$_3$): 7.47–7.28 (m, 20H); 5.31–5.03 (m, 8H); 4.32–4.18 (m, 4H); 3.19–3.15 (m, 1H); 3.16–3.12 (m, 1H); 2.86 (s, 6H); 2.00–1.90 (m, 1H); 1.89–1.79 (m, 1H); 1.64–1.49 (m, 1H); 1.48–1.38 (m, 1H); 1.37 (s, 12H); 1.36 (s, 9H); 1.32 (s, 9H); 0.9-0.8 (m, 2H); 0.41–0.3 (m, 4H); 0.15–0.05 (m, 2H); 0.04- -0.04 (m, 2H).

(vi) A solution of 3.0 g of 2,3-dibenzyl 3-tert-butyl 1-cyclopropyl-4-(3,4,4-trimethyl-2,5-dioxo-1-imidazolidinyl)-2(R),3(R,S),3-butanetricarboxylate (1:1 mixture of diastereoisomers in 30 ml of 2-propanol was hydrogenated in the presence of 0.3 g of 5% palladium on charcoal catalyst for 2 hours. The catalyst was removed by filtration and the solution was evaporated. The residue was re-evaporated from 20 ml toluene and then dissolved in 50 ml of toluene. The solution was treated with 0.693 ml of triethylamine and the mixture was heated under reflux for 2 hours. The solution was cooled to room temperature and washed with 2M hydrochoric acid, water and saturated sodium chloride solution. After drying over anhydrous magnesium suphate the solvent was evaporated to give 1.85 g of 4-tert-butyl hydrogen 2(R)-(cyclopropylmethyl)-3(R or S)-[(3,4,4-trimethyl-2,5-dioxo-1-imidazolidinyl)methyl]succinate as an approximately 6:1 mixture of diastereoisomers in the form of a yellow oil.

MS: 383 (M+H)$^+$;

Rf [dichloromethane/methanol (9:1)]=0.41.

(vii) 0.433 g of 1-hydroxybenzotriazole, 0.542 g of 1-ethyl-3-(3-dimethyl-aminopropyl)carbodiimide hydrochloride and 0.598 ml of N-ethylmorpholine were added to a stirred solution of 0.9 g of 4-tert-butyl hydrogen 2(R)-(cyclopropylmethyl)-3(R or S)-[3,4,4-trimethyl-2,5-dioxo-1-imidazolidinyl)-methyl]succinate (approximately 6:1 misture of diastereoisomers) in 10 ml of dichloromethane at 0° C. The mixture was stirred at 0° C. for 30 minutes and then a solution of 0.407 g of (S)-tert-butylglycine methylamide in 1 ml of dichloromethane was added. The mixture was stirred at 0° C. for 2 hours and then at room temperature overnight. The solution was washed with 5% sodium hydrogen carbonate solution, 2M hydrochloric acid and saturated sodium chloride solution. The solution was dried over anhydrous magnesium sulphate and evaporated to leave 1.2 g of N2-[2(R)-[1(R or S)-(tert-butoxycarbonyl)-2-(3,4,4-trimethyl-2,5-dioxo-1-imidazolidinyl)ethyl]-3-cyclopropylpropionyl]-1N,3-dimethyl-L-valinamide as a 6:1 mixture of diastereoisomers in the form of a cream foam.

MS 509 (M+H)$^+$.

Rf (5% methanol in dichloromethane)=0.55.

(viii) A solution of 1.2 g of N2-[2(R)-[1(R or S)-tert-butoxycarbonyl)-2-(3,4,4-trimethyl-2,5-dioxo-1- imidazolidinyl)ethyl]-3-cyclopropylpropionyl]-N1,3-dimethyl-L-valinamide (6:1 mixture of diastereoisomers) in 4 ml of trifluoroacetic acid was stirred at room temperature for 2 hours. The solution was evaporated and the residue was partitioned between diethyl ether and 5% sodium hydrogen carbonate. The aqueous phase was acidified with hydrochloric acid and extracted with dichloromethane. The organic layer was dried over anhydrous magnesium sulphate and evaporated to leave an oil. Trituration of the oil with hexane gave 0.65 g of N2-[2(R)-[1(R or S)-carboxy-2-(3,4,4-trimethyl-2,5-dioxo-1-imidazolidinyl)ethyl]-3-cyclopropyl-propionyl]-N1,3-dimethyl-L-valinamide as a 6:1 mixture of diastereoisomers in the form of a white solid which was used without further purification.
MS 453 (M+H)$^+$.
Rf (10% methanol in dichloromethane)=0.27.

(ix) 0.26 g of 1-hydroxybenzotriazole, 0.33 g of 1-ethyl-3-(3-dimethylamino-propyl)carbodiimide hydrochloride and 0.36 ml of N-ethylmorpholine were added to a stirred solution of 0.65 g of N2-[2(R)-[2(R or S)-carboxy-2-(3,4,4-trimethyl-2,5-dioxo-1-imidazolidinyl)ethyl[-3-cyclopropylpropionyl]-N1,3-dimethyl-L-valinamide (6:1 mixture of diastereoisomers) in 10 ml of dichloromethane at 0° C. The mixture was stirred at 0° C. for 30 minutes and then a solution of 0.21 g of O-benzylhydroxylamine in 2 ml of dichloromethane was added. The mixture was stirred at 0° C. for 2 hours and then at room temperature overnight. The solution was diluted with 50 ml of dichloromethane, washed in succession with 5% sodium hydrogen carbonate solution and 2M hydrochloric acid solution and then dried over anhydrous magnesium sulphate. The solution was evaporated and the residue was triturated with diethyl ether to give 0.47 g of N2-[2(R)-[(R or S)-(benzyloxycarbamoyl)-2-(3,4,4-trimethyl-2,5-dioxo-1-imidazolidinyl)ethyl]-3-cyclopropylpropionyl]-N1,3-dimethyl-L-valinamide as a 6:1 mixture of diastereoisomers in the form of a white solid.
nmr (d$_4$MeOH): 8.22–8.15 (m,1H); 7.5–7.36 (m,5H); 4.95–4.83 (m,2H); 3.85 (dd,J=12,8,1H); 3.53 (dd,J=12,5, 1H); 2.96–2.86 (m,4H); 2.8–2.68 (m,4H); 1.4–1.36 (m,6H); 1.35–1.25 (m,1H); 1.15–1.03 (m,10H); 0.65–0.58 (m,1H); 0.48–0.4 (m,1H); 0.37–0.31 (m,1H); 0.12- -0.03 (m,2H). MS 558 (M+H)$^+$.

EXAMPLE 5

In a manner analogous to that described in the first paragraph of Example 4, from 0.37 g of N2-[2(R)-[1(R or S)-benzyloxycarbamoyl)-2-(3,4,4-trimethyl-2,5-dioxo-1-imidazolidinyl)ethyl]-3-cyclobutylpropionyl]-N1,3-dimethyl-L-valinamide (diastereoisomer 1), prepared in a manner analogous to Example 1(i)–(ix), there was obtained 0.27 g of N2-[3-cyclobutyl-2(R)-[1(R or S)-(hydroxycarbamoyl)-2-(3,4,4-trimethyl-2,5-dioxo-1-imidazolidinyl)ethyl]propionyl]-N1,3-dimethyl-L-valinamide, diastereo-isomer 1 in the form of a white solid.
nmr (d4 MeOH): 4.19 (s,1H); 3.53(dd,J=12,10); 3.25 (dd, J=14,5); 2.75 (s,3H); 2.72–2.62 (m,4H); 2.58–2.52 (m,1H); 2.1–1.92 (m,2H); 1.85–1.27 (m,7H); 1.26 (s,6H); 0.93 (s,9H);
MS 482 (M+H)$^+$.

EXAMPLE 6

In a manner analogous to that described in the first paragraph of Example 1, from 0.326 g of N2-[2(R)-[1(R or S)-(benzyloxycarbamoyl)-4-phenylbutyl]-3-cyclobutylpropionyl]-N,3-dimethyl-L-valinamide (diastereoisomer 1), prepared in a manner analogous to that described in Example 4(v)–(ix) using 2,3-dibenzyl 3-tert-butyl 1-cyclobutyl-2(R), 3(R,S)3-propanetricarboxylate and cinnamyl bromide, there was obtained 0.246 g of N2-[3-cyclobutyl-2(R)-[1(R or S)-(hydroxycarbamoyl)-4-phenylbutyl]propionyl]-N1,3-dimethyl-L-valinamide (diastereoisomer 1) as a white solid.
nmr (d$_4$MeOH): 7.23–7.17 (m,2H); 7.13–7.07 (m,3H); 4.20 (s,1H); 2.70 (s,3H); 2.59–2.42 (m,3H); 2.24–1.99 (m,3H); 1.94–1.84 (m,1H); 1.81–1.65 (m,2H); 1.64–1.29 (m,8H); 0.94 (s,9H); MS 446 (M+H)$^+$.

EXAMPLE 7

In a manner analogous to that described in the first paragraph of Example 1, from 0.227 g of N2-[2(R)-[1(R or S)-(benzyloxycarbamoyl)4-phenylbutyl]-3-cyclopentylpropionyl]-N,3-dimethyl-L-valinamide (diastereoisomer 1), prepared in a manner analogous to that described in Example 4(v)–(ix) using 2,3-dibenzyl 3-tert-butyl 1-cyclopentyl-2(R), 3(R,S)-3-propanetricarboxylate, there was obtained 0.173 g of N2-[3-cyclopentyl-2(R)-[1(R or S)-(hydroxycarbamoyl)-4-phenylbutyl]propionyl]-N1,3-dimethyl-L-valinamide (diastereoisomer 1) as a white solid.
nmr (d$_4$MeOH): 7.23–7.16 (m,2H); 7.14–7.06 (m,3H); 4.21 (s,1H); 2.68 (s,3H); 2.63–2.49 (m,3H); 2.23–2.14 (m,1H); 1.88–1.78 (m,1H); 1.66–1.32 (m,1H); 1.24–1.16 (m,1H); 1.06–0.93 (m,11H); MS 460 (M+H)$^+$.

The following Examples illustrate pharmaceutical preparations containing the hydroxylamine derivatives provided by the present invention:

EXAMPLE A

Tablets containing the following ingredients may be produced in a conventional manner:

| Ingredient | Per tablet |
| --- | --- |
| Hydroxylamine derivative | 10.0 mg |
| Lactose | 125.0 mg |
| Corn starch | 75.0 mg |
| Talc | 4.0 mg |
| Magnesium stearate | 1.0 mg |
| Total weight | 215.0 mg |

EXAMPLE B

Capsules containing the following ingredients may be produced in a conventional manner:

| Ingredient | Per capsule |
| --- | --- |
| Hydroxylamine derivative | 10.0 mg |
| Lactose | 165.0 mg |
| Corn starch | 20.0 mg |
| Talc | 5.0 mg |
| Capsule fill weight | 200.0 mg |

We claim:
1. A compounds of the formula

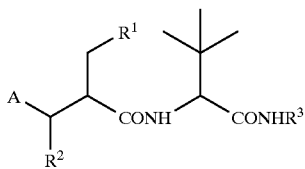 (I)

wherein
A represents a group of the formula

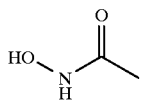 (a)

or

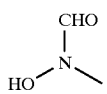 (b)

R¹ represents cyclopropyl, cyclobutyl or cyclopentyl;
R² represents hydrogen, or a group of the formula —(CH₂)$_n$-aryl, —(CH₂)$_n$-Het in which n stands for 1–4 and Het represents a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other carbon atoms by lower alkyl or oxo and/or on any additional N atom(s) by lower alkyl or aryl; and
R³ represents hydrogen or lower alkyl optionally substituted by aryl, amino, protected amino, di(lower alkyl) amino, guanidino, carboxyl, protected carboxyl, carbamoyl, pyrrolidino, piperidino or morpholino;
and pharmaceutically acceptable salts thereof.

2. The compound according to claim 1, wherein A represents a group of formula (a).

3. Compounds according to claim 1, wherein the aryl group is unsubstituted phenyl.

4. The compounds according to claim 1, wherein Het represents phthalimido or 3,4,4-trimethyl-2,5-dioxo-1-imidazolidinyl.

5. The compounds according to claim 1, wherein R³ represents unsubstituted lower alkyl.

6. The compounds according to claim 5, wherein R³ represents methyl.

7. A compound of the formula

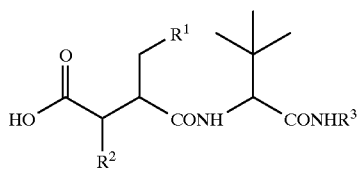 (II)

wherein
R¹ represents cyclopropyl, cyclobutyl or cyclopentyl;
R² represents hydrogen hydroxy, lower alkyl or a group of the formula —(CH₂)$_n$-aryl, —(CH₂)$_n$-Het in which n stands for 1–4 and Het represents a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other carbon atoms by lower alkyl or oxo and/or on any additional N atom(s) by lower alkyl or aryl; and
R³ represents hydrogen or lower alkyl optionally substituted by aryl, amino, protected amino, di(lower alkyl) amino, guanidino, carboxyl, protected carboxyl, carbamoyl, pyrrolidino, piperidino or morpholino.

8. A compound of the formula

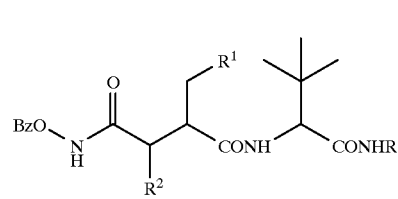 (IV)

wherein
R¹ represents cyclopropyl, cyclobutyl or cyclopentyl,
R² represents hydrogen, hydroxy, lower alkyl or a group of the formula —(CH₂)$_n$aryl, —(CH₂)$_n$-Het in which n stands for 1–4 and Het represents a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other carbon atoms by lower alkyl or oxo and/or on any additional N atom(s) by lower alkyl or aryl, and
R³ represents hydrogen or lower alkyl optionally substituted by aryl, amino, protected amino, di(lower alkyl) amino, guanidino, carboxyl, protected carboxyl, carbamoyl, pyrrolidino, piperidino or morpholino.

9. A compounds of the formula

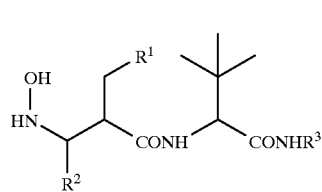 (V)

wherein
R¹ represents cyclopropyl, cyclobutyl or cyclopentyl,
R² represents hydrogen, hydroxy, lower alkyl or a group of the formula —(CH₂)$_n$-aryl, —(CH₂)$_n$-Het in which n stands for 1–4 and Het represents a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other carbon atoms by lower alkyl or oxo and/or on any additional N atom(s) by lower alkyl or aryl; and $R^3$ represents hydrogen or lower alkyl optionally substituted by aryl, amino, protected amino, di(lower alkyl) amino, guanidino, carboxyl, protected carboxyl, carbamoyl, pyrrolidino, piperidino or morpholino.

10. The compound of claim 1, wherein the compound is N2-[3-Cyclobutyl-2(R or S)-[(hydroxycarbamoyl)methyl]-propionyl]-N1,3-dimethyl-L-valinamide.

11. The compound of claim 1, wherein the compound is N2-[3-cyclopropyl-2(R or S)-[(hydroxycarbamoyl)methyl]-propionyl]-N1,3-dimethyl-L-valinamide.

12. The compound of claim 1, wherein the compound is N2-[3-Cyclopentyl-2(R or S)-[(hydroxycarbamoyl)methyl]-propionyl]-N1,3-dimethyl-L-valinamide.

13. The compound of claim 1, wherein the compound is N2-[3-Cyclobutyl-2(R)-[1(R or S)-(hydroxycarbamoyl)-4-phenyl-butyl]propionyl]-N, 1,3-dimethyl-L-valinamide.

14. The compound of claim 1, wherein the compound is N2-[3-Cyclopentyl-2(R)-[1(R or S) hydroxycarbamoyl)-4-phenylbutyl]propionyl]-N1,3-dimethyl-L-valinamide.

15. A compound of the formula

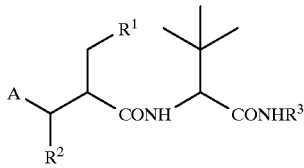
(I)

wherein
A is a group of the formula

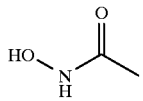
(a)

or

(b)

$R^1$ represents cyclopropyl, cyclobutyl or cyclopentyl;
$R^3$ represents hydrogen or lower alkyl optionally substituted by aryl, amino, protected amino, di(lower alkyl) amino, guanidino, carboxyl, protected carboxyl, carbamoyl, pyrrolidino, piperidino or morpholino;
$R^2$ represents —(CH$_2$)$_n$-Het in which n stands for 1–4, and Het is a group of the formula

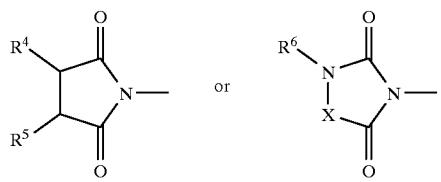 or 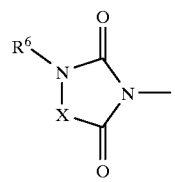

in which
$R^4$ and $R^5$ each represent hydrogen or together represent an additional bond or the remainder of a fused benzene ring;

$R^6$ represents hydrogen, lower alkyl or aryl; and
X represents —CO—, —CH$_2$—, —CH(lower alkyl)-, —C(lower alkyl)$_2$—, —NH—, —N(lower alkyl)- or —O—; or where $R^6$ represents lower alkyl and X represents —N(lower alkyl)-, the lower alkyl groups can be joined to form a 5-, 6-or 7-membered ring.

16. The compound of claim 15, wherein A represents a group of formula (a).

17. The compound of claim 15, wherein $R^3$ represents unsubstituted lower alkyl.

18. The compound of claim 17, wherein $R^3$ represents methyl.

19. The compound of claim 15, wherein the compound is N2-[3-Cyclopropyl-2(R)-[1(R or S)-(hydroxycarbamoyl)-2-(3,4,4,-trimethyl-2,5-dioxo-1-imidazolidinyl)ethyl] propionyl]-N1,3-dimethyl-L-valinamide.

20. The compound of claim 15, wherein the compound is N2-[3-Cylcobutyl-2(R)-[1(R or S)-(hydroxycarbamoyl)-2-(3,4,4-trimethyl-2,5-dioxo-1-imidazolidinyl)ethyl] propionyl]-N1,3-dimethyl-L-valinamide.

21. A compound of the formula

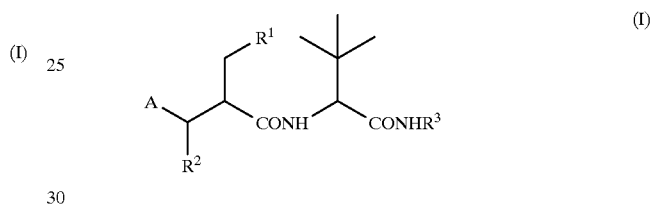
(I)

wherein
A is a group of the formula

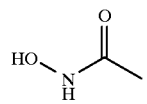
(a)

or

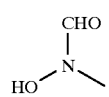
(b)

$R^1$ represents cyclopropyl, cyclobutyl or cyclopentyl;
$R^3$ represents hydrogen or lower alkyl optionally substituted by aryl, amino, protected amino, di(lower alkyl) amino, guanidino, carboxyl, protected carboxyl, carbamoyl, pyrrolidino, piperidino or morpholino; and
$R^2$ represents —(CH$_2$)$_n$-Het in which n stands for 1–4, and Het is a group of the formula

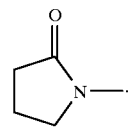

22. The compound of claim 21, wherein A represents a group of formula (a).

23. The compound of claim 21, wherein $R^3$ represents unsubstituted lower alkyl.

24. The compound of claim 23, wherein $R^3$ represents methyl.

25. A compound of the formula

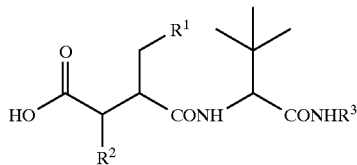
(II)

wherein
$R^1$ represents cyclopropyl, cyclobutyl or cyclopentyl;
$R^2$ represents —$(CH_2)_n$-Het in which n stands for 1–4, and Het is a group of the formula

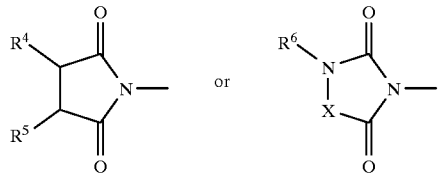

in which
$R^4$ and $R^5$ each represent hydrogen or together represent an additional bond or the remainder of a fused benzene ring;
$R^6$ represents hydrogen, lower alkyl or aryl; and
X represents —CO—, —$CH_2$—, —CH(lower alkyl)-, —C(lower alkyl)2—, —NH—, —N(lower alkyl)- or —O—; or where $R^6$ represents lower alkyl and X represents —N(lower alkyl)-, the lower alkyl groups can be joined to form a 5-, 6-or 7-membered ring; and
$R^3$ represents hydrogen or lower alkyl optionally substituted by aryl, amino, protected amino, di(lower alkyl) amino, guanidino, carboxyl, protected carboxyl, carbamoyl, pyrrolidino, piperidino or morpholino.

26. A compound of the formula

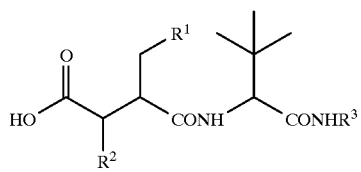
(II)

wherein
$R^1$ represents cyclopropyl, cyclobutyl or cyclopentyl;
$R^2$ represents —$(CH_2)_n$-Het in which n stands for 1–4, and Het is a group of the formula

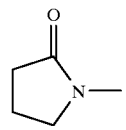

$R^3$ represents hydrogen or lower alkyl optionally substituted by aryl, amino, protected amino, di(lower alkyl) amino, guanidino, carboxyl, protected carboxyl, carbamoyl, pyrrolidino, piperidino or morpholino.

27. A compound of the formula

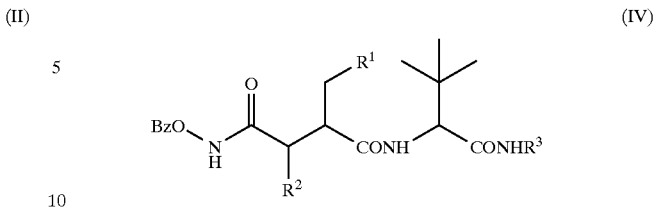
(IV)

wherein
$R^1$ represents cyclopropyl, cyclobutyl or cyclopentyl;
$R^2$ represents —$(CH_2)_n$-Het in which n stands for 1–4, and Het is a group of the formula

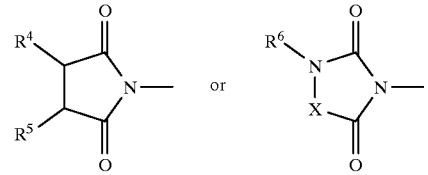

in which
$R^4$ and $R^5$ each represent hydrogen or together represent an additional bond or the remainder of a fused benzene ring;
$R^6$ represents hydrogen, lower alkyl or aryl; and
X represents —CO—, —$CH_2$—, —CH(lower alkyl)-, —C(lower alkyl)$_2$—, —NH—, —N(lower alkyl)- or —O—; or where $R^6$ represents lower alkyl and X represents -N(lower alkyl)-, the lower alkyl groups can be joined to form a 5-, 6-or 7-membered ring; and
$R^3$ represents hydrogen or lower alkyl optionally substituted by aryl, amino, protected amino, di(lower alkyl) amino, guanidino, carboxyl, protected carboxyl, carbamoyl. pyrrolidino, piperidino or morpholino.

28. A compound of the formula

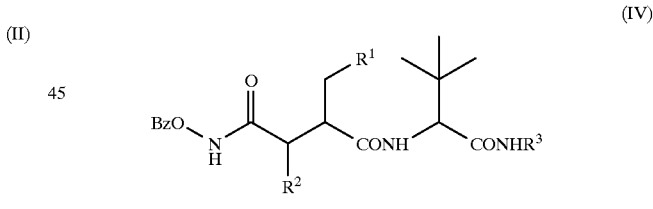
(IV)

wherein
$R^1$ represents cyclopropyl, cyclobutyl or cyclopentyl;
$R^2$ represents —$(CH_2)_n$-Het in which n stands for 1–4, and Het is a group of the formula

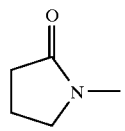
(a)

$R^3$ represents hydrogen or lower alkyl optionally substituted by aryl, amino, protected amino, di(lower alkyl) amino, guanidino, carboxyl, protected carboxyl, carbamoyl, pyrrolidino, piperidino or morpholino.

29. A compound of the formula

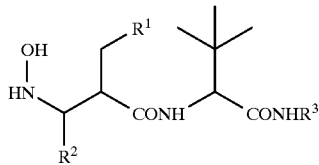
(V)

wherein

R¹ represents cyclopropyl, cyclobutyl or cyclopentyl;

R² represents —(CH$_2$)$_n$-Het in which n stands for 1–4, and Het is a group of the formula

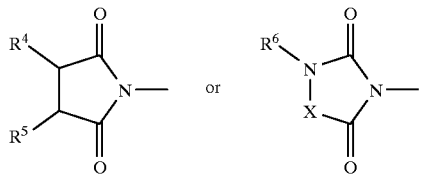

in which

R⁴ and R⁵ each represent hydrogen or together represent an additional bond or the remainder of a fused benzene ring;

R⁶ represents hydrogen, lower alkyl or aryl; and

X represents —CO—, —CH$_2$—, —CH(lower alkyl)-, —C(lower alkyl)2—, —NH—, —N(lower alkyl)- or —O—; or where R⁶ represents lower alkyl and X represents —N(lower alkyl)-, the lower alkyl groups can be joined to form a 5-, 6-or 7-membered ring; and R³ represents hydrogen or lower alkyl optionally substituted by aryl, amino, protected amino, di(lower alkyl) amino, guanidino, carboxyl, protected carboxyl, carbamoyl, pyrrolidino, piperidino or morpholino.

30. A compound of the formula

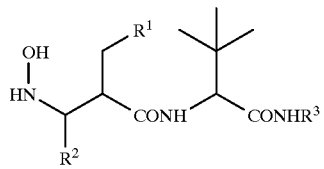
(V)

wherein

R¹ represents cyclopropyl, cyclobutyl or cyclopentyl;

R² represents —(CH$_2$)$_n$-Het in which n stands for 1–4, and Het is a group of the formula

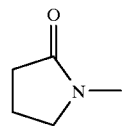

R³ represents hydrogen or lower alkyl optionally substituted by aryl, amino, protected amino, di(lower alkyl) amino, guanidino, carboxyl, protected carboxyl, carbamoyl, pyrrolidino, piperidino or morpholino.

31. A process for producing a compound of formula:

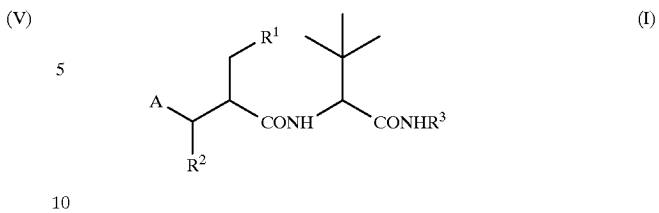
(I)

wherein

A is a group of the formula

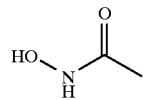
(a)

or

(b)

R¹ represents cyclopropyl, cyclobutyl or cyclopentyl;

R² represents hydrogen, hydroxy, lower alkyl or a group of the formula —(CH$_2$)$_n$-aryl, —(CH$_2$)$_n$-Het in which n stands for 1–4 and Het represents a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other carbon atoms by lower alkyl or oxo and/or on any additional N atom(s) by lower alkyl or aryl; and R³ represents hydrogen or lower alkyl optionally substituted by aryl, amino, protected amino, di(lower alkyl) amino, guanidino, carboxyl, protected carboxyl, carbamoyl, pyrrolidino, piperidino or morpholino;

comprising reacting an acid of formula

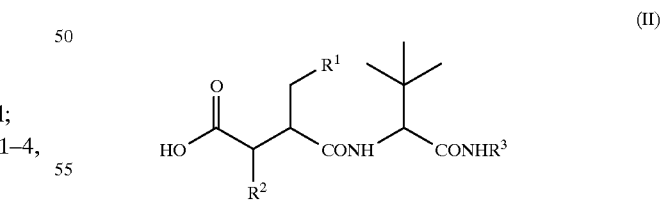
(II)

with a compound of formula H$_2$NOZ, wherein Z is hydrogen, tri(lower alkyl)silyl or diphenyl (lower alkyl)silyl, and if Z is diphenyl(lower alkyl)silyl subsequently cleaving off any diphenyl(lower alkyl) silyl group present in the product of the reaction of the acid with the compound of formula H$_2$NOZ, thereby producing the compound of formula I.

32. A process for producing a compound of formula:

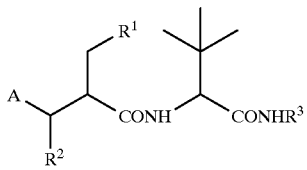 (I)

wherein

A is a group of the formula

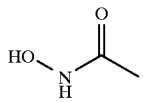 (a)

or

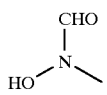 (b)

$R^1$ represents cyclopropyl, cyclobutyl or cyclopentyl;
$R^2$ represents hydrogen, hydroxy, lower alkyl or a group of the formula —$(CH_2)_n$-aryl, —$(CH_2)_n$-Het in which n stands for 1–4 and Het represents a 5- or 6-membered N-heterocyclic ring which (a) is attached via the N atom, (b) optionally contains N, O and/or S as additional hetero atom(s) in a position or positions other than adjacent to the linking N atom, (c) is substituted by oxo on one or both C atoms adjacent to the linking N atom and (d) is optionally benz-fused or optionally substituted on one or more other carbon atoms by lower alkyl or oxo and/or on any additional N atom(s) by lower alkyl or aryl; and $R^3$ represents hydrogen or lower alkyl optionally substituted by aryl, amino, protected amino, di(lower alkyl) amino, guanidino, carboxyl, protected carboxyl, carbamoyl, pyrrolidino, piperidino or morpholino;

comprising catalytically hydrogenating a compound of formula

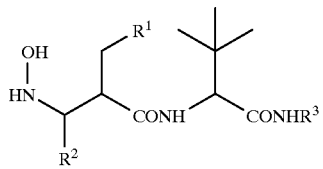 (V)

wherein Bz is benzyl,
thereby producing the compound of formula I.

* * * * *

UNITED STATES PATENT AND TRADEMARK OFFICE
CERTIFICATE OF CORRECTION

PATENT NO. : 6,066,662
DATED : May 23, 2000
INVENTOR(S) : Michael John Broadhurst, Paul Anthony Brown, William Henry Johnson It is certified that error appears in the above-identified patent and that said Letters Patent is hereby corrected as shown below:

Title Page,

Column 1,
Item [86] "§ 371 Date: Nov. 2, 1996
    § 102(e) Date: Nov. 2, 1996" should be -- § 371 Date: Nov. 20, 1996
       § 102(e) Date: Nov. 20, 1996 --

Column 19,
Line 2, "A compounds" should be -- A compound --
Line 48, "The compounds" should be -- The compound --
Line 51, "The compounds" should be -- The compound --
Line 53, "The compounds" should be -- The compound --

Column 20,
Line 1, "$R^2$ represents hydrogen hydroxy," should be
-- $R^2$, represents hydrogen, hydroxy, --
Line 29, "or cyclopentyl, "should be -- or cyclopentyl; --
Line 31, -$(CH_2)_n$aryl," should be -- -$(CH_2)_n$-aryl, --
Line 42, "or aryl, and" should be -- or aryl; and --
Line 47, "A compounds" should be -- A compound --
Line 59, "or cyclopentyl," should be -- or cyclopentyl; --

UNITED STATES PATENT AND TRADEMARK OFFICE
CERTIFICATE OF CORRECTION

PATENT NO. : 6,066,662
DATED : May 23, 2000
INVENTOR(S) : Michael John Broadhurst, Paul Anthony Brown, William Henry Johnson It is certified that error appears in the above-identified patent and that said Letters Patent is hereby corrected as shown below:

Column 23,
Line 32, "-C(lower alkyl)2-," should be -- -C(lower alkyl)$_2$-, --

Signed and Sealed this

Seventh Day of August, 2001

*Attest:*

*Attesting Officer*

NICHOLAS P. GODICI
*Acting Director of the United States Patent and Trademark Office*